US012011528B2

(12) United States Patent
Buckberry et al.

(10) Patent No.: US 12,011,528 B2
(45) Date of Patent: Jun. 18, 2024

(54) PHASED CONVECTIVE OPERATION

(71) Applicant: Quanta Dialysis Technologies Ltd., Warwickshire (GB)

(72) Inventors: Clive Buckberry, Warwickshire (GB); Keith Heyes, Warwickshire (GB); Eduardo Esser, Warwickshire (GB)

(73) Assignee: QUANTA DIALYSIS TECHNOLOGIES LTD., Warwickshire (GB)

(*) Notice: Subject to any disclaimer, the term of this patent is extended or adjusted under 35 U.S.C. 154(b) by 1148 days.

(21) Appl. No.: 16/483,345

(22) PCT Filed: Feb. 2, 2018

(86) PCT No.: PCT/GB2018/050308
§ 371 (c)(1),
(2) Date: Aug. 2, 2019

(87) PCT Pub. No.: WO2018/142153
PCT Pub. Date: Aug. 9, 2018

(65) Prior Publication Data
US 2019/0374698 A1 Dec. 12, 2019

(30) Foreign Application Priority Data
Feb. 2, 2017 (GB) ...................... 1701740

(51) Int. Cl.
*A61M 1/26* (2006.01)
*A61M 1/14* (2006.01)
(Continued)

(52) U.S. Cl.
CPC ............ *A61M 1/267* (2014.02); *A61M 1/155* (2022.05); *A61M 1/156* (2022.05);
(Continued)

(58) Field of Classification Search
CPC .......... A61M 1/14; A61M 1/15; A61M 1/267; A61M 1/3401; A61M 1/3413; A61M 39/22; A61M 39/227; A61M 2205/128
See application file for complete search history.

(56) References Cited

U.S. PATENT DOCUMENTS 2,696,173 A    12/1954 Thormod
3,338,171 A    8/1967 Conklin et al.
(Continued)

FOREIGN PATENT DOCUMENTS

CA            81430        8/1997
DE        10024447 A1    11/2001
(Continued)

OTHER PUBLICATIONS

He et al., "A Fluorescent Sensor with High Selectivity and Sensitivity for Potassium in Water," Journal of the American Chemical Society 2003 125 (6), 1468-1469.
(Continued)

*Primary Examiner* — Philip R Wiest
(74) *Attorney, Agent, or Firm* — THE MARBURY LAW GROUP, PLLC

(57) ABSTRACT

The invention provides a blood treatment device comprising: a dialyser; an inlet pump assembly; an outlet pump assembly; and a control system. The inlet pump assembly configured to deliver a first volume of dialysate from a dialysate source to the dialyser in an inlet pump cycle having a dialysate delivery stroke. The outlet pump assembly configured to remove a second volume of dialysate from the dialyser and deliver the dialysate away from the dialyser in an outlet pump cycle having a dialysate removal stroke. The control system is configured to operate the inlet pump assembly in the inlet pump cycle, and configured to operate the outlet pump assembly in the outlet pump cycle. For each inlet pump cycle there is a corresponding outlet pump cycle,
(Continued)

and each inlet pump assembly dialysate delivery stroke has a commencement time $t_1$ and a termination time h, and each outlet pump assembly dialysate removal stroke has a commencement time $t_3$ and a termination time $t_4$. The blood treatment device is operable such that either: each dialysate removal stroke commencement time $t_3$ is after the respective corresponding dialysate delivery stroke commencement time ti and before the respective corresponding dialysate delivery stroke termination time $t_2$; or each dialysate delivery stroke commencement time $t_1$ is after the respective corresponding dialysate removal stroke commencement time $t_3$ and before the respective corresponding dialysate removal stroke termination time $t_4$.

23 Claims, 8 Drawing Sheets

(51) Int. Cl.
A61M 1/34 (2006.01)
A61M 39/22 (2006.01)
(52) U.S. Cl.
CPC ...... *A61M 1/15625* (2022.05); *A61M 1/1565* (2022.05); *A61M 1/3413* (2013.01); *A61M 39/22* (2013.01); *A61M 2205/128* (2013.01)

(56) References Cited

U.S. PATENT DOCUMENTS

| | | |
|---|---|---|
| 3,468,261 A | 9/1969 | Schmierer |
| 3,605,566 A | 9/1971 | Vetter |
| 3,606,592 A | 9/1971 | Madurski et al. |
| 3,753,493 A | 8/1973 | Mellor |
| 3,774,762 A | 11/1973 | Lichtenstein |
| 3,807,906 A | 4/1974 | Breit |
| 3,921,622 A | 11/1975 | Cole |
| 3,972,320 A | 8/1976 | Kalman |
| 4,070,725 A | 1/1978 | Cornelius |
| 4,142,845 A | 3/1979 | Lepp et al. |
| 4,161,264 A | 7/1979 | Malmgren |
| 4,205,686 A | 6/1980 | Harris et al. |
| 4,353,990 A | 10/1982 | Manske et al. |
| 4,366,061 A * | 12/1982 | Papanek ............ A61M 1/1615 210/188 |
| 4,368,261 A | 1/1983 | Klose et al. |
| 4,370,983 A | 2/1983 | Lichtenstein |
| 4,430,048 A | 2/1984 | Fritsch |
| 4,494,912 A | 1/1985 | Pauliukonis |
| D277,991 S | 3/1985 | Becker |
| 4,534,755 A | 8/1985 | Calvert et al. |
| 4,534,756 A | 8/1985 | Nelson |
| 4,546,669 A | 10/1985 | Fischer et al. |
| 4,564,342 A | 1/1986 | Weber et al. |
| 4,599,165 A | 7/1986 | Chevallet |
| 4,648,869 A | 3/1987 | Bobo, Jr. |
| 4,666,598 A | 5/1987 | Heath et al. |
| 4,710,163 A | 12/1987 | Butterfield |
| 4,771,792 A | 9/1988 | Seale |
| 4,828,543 A | 5/1989 | Weiss et al. |
| 4,897,184 A | 1/1990 | Shouldice et al. |
| D308,249 S | 5/1990 | Buckley |
| 4,969,991 A | 11/1990 | Valadez |
| 5,000,664 A | 3/1991 | Lawless et al. |
| 5,012,197 A | 4/1991 | Seiffert et al. |
| 5,032,265 A | 7/1991 | Jha et al. |
| 5,055,198 A | 10/1991 | Shettigar |
| 5,095,910 A | 3/1992 | Powers |
| 5,103,211 A | 4/1992 | Daoud et al. |
| 5,126,831 A | 6/1992 | Nakagawara |
| 5,232,434 A | 8/1993 | Inagaki et al. |
| 5,252,213 A | 10/1993 | Ahmad et al. |
| D341,890 S | 11/1993 | Sievert et al. |
| D344,339 S | 2/1994 | Yoshikawa et al. |
| 5,304,349 A | 4/1994 | Polaschegg |
| D347,896 S | 6/1994 | Dickinson et al. |
| D351,470 S | 10/1994 | Scherer et al. |
| 5,385,540 A | 1/1995 | Abbott et al. |
| 5,421,823 A | 6/1995 | Kamen et al. |
| 5,458,468 A | 10/1995 | Ye et al. |
| 5,476,368 A | 12/1995 | Rabenau et al. |
| 5,476,792 A | 12/1995 | Ezrielev et al. |
| D370,979 S | 6/1996 | Pascale et al. |
| 5,558,347 A | 9/1996 | Nicholson |
| 5,586,872 A | 12/1996 | Skobelev et al. |
| 5,586,873 A | 12/1996 | Novak et al. |
| 5,591,344 A | 1/1997 | Kenley et al. |
| 5,643,201 A | 7/1997 | Peabody et al. |
| 5,650,071 A | 7/1997 | Brugger et al. |
| 5,653,456 A | 8/1997 | Mough |
| 5,658,456 A | 8/1997 | Kenley et al. |
| 5,665,307 A | 9/1997 | Kirschner et al. |
| 5,727,550 A | 3/1998 | Montecalvo |
| D395,085 S | 6/1998 | Kenley et al. |
| 5,788,851 A | 8/1998 | Kenley et al. |
| 5,807,322 A | 9/1998 | Lindsey et al. |
| 5,882,300 A | 3/1999 | Malinouskas et al. |
| 5,948,247 A | 9/1999 | Gillerfaik et al. |
| 5,957,670 A | 9/1999 | Duncan et al. |
| 5,995,910 A | 11/1999 | Discenzo |
| 6,077,443 A | 6/2000 | Goldau |
| 6,126,831 A | 10/2000 | Goldau et al. |
| 6,132,378 A | 10/2000 | Marino |
| 6,143,181 A | 11/2000 | Falkvall et al. |
| 6,153,102 A | 11/2000 | Kenley et al. |
| 6,216,029 B1 | 4/2001 | Paltieli |
| 6,218,329 B1 | 4/2001 | Singh et al. |
| 6,251,279 B1 | 6/2001 | Peterson et al. |
| 6,261,065 B1 | 7/2001 | Nayak et al. |
| 6,303,036 B1 | 10/2001 | Collins et al. |
| 6,382,923 B1 | 5/2002 | Gray |
| 6,514,462 B1 | 2/2003 | Simons |
| 6,558,347 B1 | 5/2003 | Jhuboo et al. |
| 6,582,206 B2 | 6/2003 | Schluecker |
| 6,626,832 B1 | 9/2003 | Paltieli et al. |
| 6,626,878 B1 | 9/2003 | Leisner et al. |
| 6,645,176 B1 | 11/2003 | Christenson et al. |
| 6,663,829 B1 | 12/2003 | Kjellstrand |
| 6,733,476 B2 | 5/2004 | Christenson et al. |
| 6,743,204 B2 | 6/2004 | Christenson et al. |
| 6,801,646 B1 | 10/2004 | Pena et al. |
| 6,814,547 B2 | 11/2004 | Childers et al. |
| 6,967,002 B1 | 11/2005 | Edgson et al. |
| 7,040,142 B2 | 5/2006 | Burbank |
| 7,107,837 B2 | 9/2006 | Lauman et al. |
| 7,153,286 B2 | 12/2006 | Busby et al. |
| 7,220,358 B2 | 5/2007 | Schacht et al. |
| 7,284,964 B2 | 10/2007 | McDowell et al. |
| 7,383,721 B2 | 6/2008 | Parsons et al. |
| 7,434,312 B2 | 10/2008 | Christenson et al. |
| 7,494,590 B2 | 2/2009 | Felding et al. |
| 7,604,398 B1 | 10/2009 | Akers et al. |
| 7,648,627 B2 | 1/2010 | Beden et al. |
| 7,857,976 B2 | 12/2010 | Bissier et al. |
| 7,874,999 B2 | 1/2011 | Busby |
| 7,896,197 B2 | 3/2011 | Furey et al. |
| D641,882 S | 7/2011 | Hickey et al. |
| 8,114,043 B2 | 2/2012 | Muller |
| 8,132,388 B2 | 3/2012 | Nagy et al. |
| 8,137,184 B2 | 3/2012 | Ajiro et al. |
| 8,137,300 B2 | 3/2012 | Han et al. |
| 8,167,431 B2 | 5/2012 | DeCusatis et al. |
| 8,187,184 B2 | 5/2012 | Muller et al. |
| 8,192,388 B2 | 6/2012 | Hogard |
| 8,197,431 B2 | 6/2012 | Bennison |
| 8,221,320 B2 | 7/2012 | Bouton |
| 8,348,850 B2 | 1/2013 | Frinak et al. |
| 8,360,977 B2 | 1/2013 | Marttila et al. |
| 8,529,490 B2 | 9/2013 | Warlar et al. |
| 8,535,522 B2 | 9/2013 | Fulkerson et al. |
| 8,535,525 B2 | 9/2013 | Heyes et al. |
| D693,469 S | 11/2013 | Chung et al. |

(56) References Cited

U.S. PATENT DOCUMENTS

| | | | |
|---|---|---|---|
| 8,597,505 B2 | 12/2013 | Fulkerson et al. |
| D702,842 S | 4/2014 | Hyde et al. |
| 8,685,244 B2 | 4/2014 | Heyes et al. |
| 8,696,571 B2 | 4/2014 | Marttila et al. |
| 8,708,908 B2 | 4/2014 | Bouton |
| 8,708,946 B2 | 4/2014 | Han et al. |
| D705,432 S | 5/2014 | Lura et al. |
| 8,798,908 B2 | 8/2014 | Bourdeaut |
| 8,801,646 B2 | 8/2014 | Han et al. |
| D714,454 S | 9/2014 | Amemiya et al. |
| D714,946 S | 10/2014 | Lura et al. |
| 8,926,544 B2 | 1/2015 | Hogard et al. |
| D724,740 S | 3/2015 | Collins et al. |
| 8,974,394 B2 | 3/2015 | Frinak et al. |
| 9,011,334 B2 | 4/2015 | Bouton |
| D735,868 S | 8/2015 | Mareguddi et al. |
| 9,220,825 B2 | 12/2015 | Buckberry |
| D781,410 S | 3/2017 | Ritter et al. |
| 9,744,285 B2 | 8/2017 | Heyes et al. |
| 9,833,553 B2 | 12/2017 | Higgitt et al. |
| 10,456,516 B2 | 10/2019 | Heyes et al. |
| D867,597 S | 11/2019 | Bauer et al. |
| 10,543,305 B2 | 1/2020 | Buckberry et al. |
| D879,967 S | 3/2020 | Verguldi et al. |
| D907,211 S | 1/2021 | Spurling |
| 10,881,775 B2 | 1/2021 | Wallace |
| 10,960,120 B2 | 3/2021 | Wallace et al. |
| D924,410 S | 7/2021 | Mendoza et al. |
| D938,046 S | 12/2021 | Gupta et al. |
| 11,365,728 B2 | 6/2022 | Westenbrink |
| 11,571,499 B2 | 2/2023 | Milad et al. |
| 11,583,618 B2 | 2/2023 | Buckberry et al. |
| 2003/0217962 A1 | 11/2003 | Childers et al. |
| 2004/0195157 A1 | 10/2004 | Mullins et al. |
| 2004/0206703 A1 | 10/2004 | Bosetto et al. |
| 2004/0215129 A1 | 10/2004 | Edgson et al. |
| 2004/0223857 A1 | 11/2004 | Kline |
| 2005/0020961 A1 | 1/2005 | Burbank et al. |
| 2005/0205476 A1 | 9/2005 | Chevallet et al. |
| 2005/0209547 A1 | 9/2005 | Burbank et al. |
| 2005/0234384 A1 | 10/2005 | Westberg |
| 2006/0121623 A1 | 6/2006 | He et al. |
| 2007/0083193 A1 | 4/2007 | Werneth et al. |
| 2008/0006089 A1 | 1/2008 | Adnan et al. |
| 2008/0200865 A1 | 8/2008 | Bedingfield |
| 2008/0283096 A1 | 11/2008 | Scheringer et al. |
| 2009/0001245 A1 | 1/2009 | Childers et al. |
| 2009/0007642 A1 | 1/2009 | Busby et al. |
| 2009/0009290 A1 | 1/2009 | Kneip et al. |
| 2009/0012450 A1 | 1/2009 | Shah et al. |
| 2009/0012452 A1 | 1/2009 | Slepicka et al. |
| 2009/0012457 A1* | 1/2009 | Childers ............ A61M 1/288 604/29 |
| 2009/0101550 A1 | 4/2009 | Muller et al. |
| 2009/0211975 A1 | 8/2009 | Brugger et al. |
| 2009/0230043 A1 | 9/2009 | Heyes et al. |
| 2010/0043694 A1 | 2/2010 | Patel |
| 2010/0045471 A1 | 2/2010 | Meyers |
| 2010/0089807 A1 | 4/2010 | Heyes et al. |
| 2010/0139254 A1 | 6/2010 | Sebestyen et al. |
| 2010/0263687 A1 | 10/2010 | Braun et al. |
| 2011/0009797 A1 | 1/2011 | Kelly et al. |
| 2011/0034850 A1 | 2/2011 | Jonsson |
| 2011/0132838 A1 | 6/2011 | Curtis et al. |
| 2011/0168614 A1 | 7/2011 | Pouchoulin et al. |
| 2012/0164022 A1 | 6/2012 | Muginstein et al. |
| 2012/0269907 A1 | 10/2012 | Coates |
| 2012/0276549 A1 | 11/2012 | Cunningham et al. |
| 2012/0292237 A1 | 11/2012 | Heyes et al. |
| 2012/0308431 A1 | 12/2012 | Kotsos et al. |
| 2013/0037465 A1 | 2/2013 | Heyes et al. |
| 2013/0056419 A1 | 3/2013 | Curtis |
| 2013/0153495 A1 | 6/2013 | Kelly et al. |
| 2013/0199998 A1 | 8/2013 | Kelly et al. |
| 2013/0274642 A1 | 10/2013 | Soykan et al. |
| 2014/0224736 A1 | 8/2014 | Heide |
| 2014/0251885 A1 | 9/2014 | Heyes |
| 2014/0271106 A1 | 9/2014 | Alessandro et al. |
| 2014/0299544 A1 | 10/2014 | Wilt et al. |
| 2015/0027951 A1 | 1/2015 | Wallace et al. |
| 2015/0076053 A1 | 3/2015 | Higgitt et al. |
| 2015/0112119 A1 | 4/2015 | Buckberry |
| 2015/0129481 A1 | 5/2015 | Higgitt et al. |
| 2015/0238673 A1 | 8/2015 | Gerber et al. |
| 2015/0258263 A1 | 9/2015 | Hogard |
| 2015/0352269 A1 | 12/2015 | Gerber et al. |
| 2015/0359954 A1 | 12/2015 | Gerber et al. |
| 2016/0045656 A1 | 2/2016 | Buckberry |
| 2016/0051743 A1 | 2/2016 | Buckberry |
| 2016/0058933 A1 | 3/2016 | Ballantyne et al. |
| 2016/0076535 A1 | 3/2016 | Clifton et al. |
| 2016/0077644 A1 | 3/2016 | Ritter et al. |
| 2016/0199558 A1* | 7/2016 | Buckberry ............ A61M 1/168 210/636 |
| 2017/0056576 A1 | 3/2017 | Doyle et al. |
| 2017/0167983 A1 | 6/2017 | Klomp et al. |
| 2017/0252498 A1 | 9/2017 | Heyes et al. |
| 2017/0296730 A1 | 10/2017 | Soto et al. |
| 2018/0133391 A1 | 5/2018 | Heyes et al. |
| 2018/0154059 A1 | 6/2018 | Heyes et al. |
| 2018/0193545 A1 | 7/2018 | Crnkovich et al. |
| 2018/0344915 A1 | 12/2018 | Wallace |
| 2019/0001042 A1 | 1/2019 | Buckberry |
| 2019/0015577 A1 | 1/2019 | Garrido et al. |
| 2019/0024654 A1 | 1/2019 | May et al. |
| 2019/0358381 A1 | 11/2019 | Westenbrink |
| 2019/0376504 A1 | 12/2019 | Westenbrink |
| 2019/0385434 A1 | 12/2019 | Yuds et al. |
| 2020/0030515 A1 | 1/2020 | Merchant |
| 2020/0075159 A1 | 3/2020 | Bardorz et al. |
| 2020/0268958 A1 | 8/2020 | Heyes et al. |
| 2020/0276372 A1 | 9/2020 | Milad et al. |
| 2020/0330671 A1 | 10/2020 | Buckberry et al. |
| 2021/0110920 A1 | 4/2021 | Heyes et al. |
| 2022/0001087 A1 | 1/2022 | Heyes et al. |
| 2022/0160943 A9 | 5/2022 | Buckberry et al. |
| 2022/0241480 A1 | 8/2022 | Fincham |
| 2022/0241573 A1 | 8/2022 | Fincham |

FOREIGN PATENT DOCUMENTS

| | | |
|---|---|---|
| EP | 0165751 A2 | 12/1985 |
| EP | 0754468 A2 | 1/1997 |
| EP | 2219703 A1 | 8/2010 |
| EP | 2955512 A1 | 12/2015 |
| EP | 004375764-0001 | 10/2017 |
| EP | 004375764-0002 | 10/2017 |
| EP | 007955125-0002 | 6/2020 |
| FR | 2 310 136 | 12/1976 |
| GB | 9007955125-0001 | 5/2020 |
| GB | 9007955125-0002 | 5/2020 |
| JP | H04266740 | 9/1992 |
| JP | H06261872 | 9/1994 |
| JP | H07174659 | 7/1995 |
| JP | 2000/130334 | 5/2000 |
| JP | D1645323 | 11/2020 |
| WO | WO 81/01800 | 7/1981 |
| WO | WO 91/00113 | 1/1991 |
| WO | WO 91/16542 | 10/1991 |
| WO | WO 95/06205 | 3/1995 |
| WO | WO 95/25893 | 9/1995 |
| WO | WO 96/25214 | 8/1996 |
| WO | WO 97/10013 | 3/1997 |
| WO | WO 97/28368 | 8/1997 |
| WO | WO 99/29356 | 6/1999 |
| WO | WO 2000/006217 | 2/2000 |
| WO | WO 00/57935 | 10/2000 |
| WO | WO 02/066833 | 8/2002 |
| WO | WO 02/081917 | 10/2002 |
| WO | WO 2003/101510 | 12/2003 |
| WO | WO 2005/044339 | 5/2005 |

(56) References Cited

FOREIGN PATENT DOCUMENTS

| | | |
|---|---|---|
| WO | WO 2005/080794 | 9/2005 |
| WO | WO 2006/120415 | 11/2006 |
| WO | WO 2006/120417 | 11/2006 |
| WO | WO 2008/100671 | 8/2008 |
| WO | WO 2008/106191 | 9/2008 |
| WO | WO 2008/135245 | 11/2008 |
| WO | WO 2009/006489 | 1/2009 |
| WO | WO 2009/024333 | 2/2009 |
| WO | WO 2009/038834 | 3/2009 |
| WO | 2009061608 A1 | 5/2009 |
| WO | WO 2009/127624 | 10/2009 |
| WO | WO 2010/089130 | 8/2010 |
| WO | WO 2010/146343 | 12/2010 |
| WO | WO 2011/027118 | 3/2011 |
| WO | WO 2011/068885 | 6/2011 |
| WO | WO 2011/105697 | 9/2011 |
| WO | WO 2011/105698 | 9/2011 |
| WO | WO 2013/052680 | 4/2013 |
| WO | WO 2013/057109 | 4/2013 |
| WO | 2013110919 A1 | 8/2013 |
| WO | WO 2013/110906 | 8/2013 |
| WO | WO 2013/114063 | 8/2013 |
| WO | WO 2013/121162 | 8/2013 |
| WO | WO 2013/121163 | 8/2013 |
| WO | WO 2014/072195 | 5/2014 |
| WO | WO 2014/082855 | 6/2014 |
| WO | WO 2014/155121 | 10/2014 |
| WO | WO 2015/007596 | 1/2015 |
| WO | 2015022537 A1 | 2/2015 |
| WO | WO 2016/016870 | 2/2016 |
| WO | WO 2017/137723 | 8/2017 |
| WO | WO 2018/115816 | 6/2018 |

OTHER PUBLICATIONS

Kivi, Air Embolism, Healthline, Aug. 20, 2012, p. 1-5.

Search Report and Written Opinion for International Application No. PCT/GB2018/050308, dated Apr. 26, 2018.

Ergo-Express Motorized Dialysis Cart, Aug. 14, 2017, youtube.com [online], [site visited Jan. 9, 2022], Available from internet, URL: <https://www.youtube.com/watch?v=j4rAXthOmbY> (Year: 2017).

Home Dialysis Tescon Aqua Tech, Aug. 1, 2020, youtube.com [online], [site visited Jan. 9, 2022], Available from internet, URL: <https://www.youtube.com/watch?v=WLLPZoS_mz4> (Year: 2020).

LHO2028 Portable Hemodialysis Machine, date unknown, aliexpress.com [online], [site visited Jan. 4, 2022], Available from internet: <https://www.aliexpress.com/item/1005003324875329.html?randl_currency=USD&_randl_shipto=US&src=google&afffcid=1003bab3b8db4e93b9ba88522a14cfc1-1641319351626-05232-UneMJZVf&aff_fsk=UneMJZVf&aff_platform=aaf&sk=UneMJZVf&aff_trace_key= (Year: 2022).

Medical Hemodialysis Machine, date unknown, aliexpress.com [online], [site visited Jan. 4, 2022], Available from internet: <https://www.aliexpress.com/item/1005003445721549.html?_randl_currency=USD&_randl_shipto=US&src=google&aff_fcid=a524f3f9cd9b4976b6b47962f3439d62-1641319166409-02691-UneMJZVf&aff_fsk=UneMJZVf&aff_platform=aaf&sk=UneMJZVf&aff_trace_key=a524f3f9cd9b4976b6b47962f3439d62-1641319166409-02691-UneMJZVf&terminal_id=d0c2cca4b7664d128cb4801 a9ef03ff2> (Year: 2022).

Millenium HX Portable Dialysis Water System, Jul. 2, 2014, youtube.com [online], [site visited Jan. 10, 2022], Available from internet, URL: <https://www.youtube.com/watch?v=IGEbPi2CDsw> (Year: 2014).

Portable home dialysis device, Nov. 2, 2017, med-technews.com [online], [site visited Jan. 4, 2022], Available from internet: <https://www.med-technews.com/news/portable-home-dialysis-device-to-launch-next-year/ (Year: 2017).

\* cited by examiner

PHASED CONVECTIVE OPERATION

This application is a National Stage Entry entitled to and hereby claiming priority under 35 U.S.C. §§ 365 and 371 to corresponding PCT Application No. PCT/GB2018/050308, filed Feb. 2, 2018 entitled "Phased Convective Operation", which in turn claims priority to G.B. Patent Application No.: 1701740.1, filed Feb. 2, 2017, entitled the same. The disclosures of the above applications are incorporated herein by reference in their entireties.

FIELD OF THE INVENTION

The present invention relates to convective operation of a blood treatment device, and in particular to a convective operation method providing user control and potential for tailoring.

BACKGROUND TO THE INVENTION

Patients suffering from reduced kidney function rely on external blood treatments to remove harmful waste substances that build up in their blood over time. One of the most common methods of treatment is haemodialysis. An example of haemodialysis is set out in the applicant's previous application WO2015/022537.

Haemodialysis typically involves two networks of fluid passageways running adjacent to one another in a counter-current flow arrangement. Blood is passed through one set of tubules and dialysate is passed through the other. The pH and osmotic potential of the dialysate is adapted such that waste compounds built up in the blood diffuse from the blood into the dialysate through a semi-permeable membrane which separates the blood and dialysate sides of the network of fluid passageways.

Haemodialysis provides a method of gradually removing waste materials with a molecular weight from 50 to 60000 Daltons from the blood by diffusion, minimising fatigue to the patient. However, there are some disadvantages associated with haemodialysis.

One disadvantage of haemodialysis is that medium molecular weight molecules (mMVV) dissolved in the blood (for example β-2 microglobulin), which are typically between 1000 and 15000 Daltons, are difficult to remove completely from the blood using haemodialysis. It can take a long time to reduce the levels of these substances in the blood to acceptable levels, which may not be convenient for a patient. One other disadvantage of haemodialysis is that molecules can become attached to the semi-permeable membrane, causing a film to build up on the membrane over time. This is detrimental to the operation of the device.

An alternative approach to remove waste molecules from the blood is to use a form of convective operation, such as haemodiafiltration.

Classically, haemodiafiltration involves administering sterile dialysate to the blood either by employing a large hydrostatic potential to force sterile dialysate across a semi-permeable membrane into the blood or by directly adding it to the blood; and then pulling the sterile dialysate, complete with dissolved waste products, back across the semi-permeable membrane for subsequent disposal. This type of blood treatment is not limited by diffusion, as sterile dialysate is allowed to mix directly with the blood and returned to the dialysate by a process termed "solute drag".

One known haemodiafiltration method of directly adding dialysate to the blood is controlled by infusing the blood side of the dialyser with sterile solution at a constant flow rate. However, increased patient monitoring may be necessary, and this type of treatment may not suit all patients.

An example of haemodiafiltration is also set out in the applicant's previous application WO2015/022537, the contents of which are incorporated herein by reference.

Known methods may not allow much control over, or tailoring of, the infusion. Known methods may require extra haemodiafiltration dialysate preparation steps, extra haemodiafiltration dialysate filtration and sterilisation steps, and an additional pump or pumps to move the dialysate independently of the blood pump or pumps.

There is therefore a need for improvements in blood treatment methods and devices.

SUMMARY OF THE INVENTION

According to a first aspect of the invention, there is provided a blood treatment device comprising: a dialyser; an inlet pump assembly configured to deliver a first volume of dialysate from a dialysate source to the dialyser in an inlet pump cycle having a dialysate delivery stroke; an outlet pump assembly configured to remove a second volume of dialysate from the dialyser and deliver the dialysate away from the dialyser in an outlet pump cycle having a dialysate removal stroke; and a control system configured to operate the inlet pump assembly in the inlet pump cycle, and configured to operate the outlet pump assembly in the outlet pump cycle, wherein for each inlet pump cycle there is a corresponding outlet pump cycle, wherein each inlet pump assembly dialysate delivery stroke has a commencement time $t_1$ and a termination time $t_2$, each outlet pump assembly dialysate removal stroke has a commencement time $t_3$ and a termination time $t_4$, and either: each dialysate removal stroke commencement time $t_3$ is after the respective corresponding dialysate delivery stroke commencement time $t_1$ and before the respective corresponding dialysate delivery stroke termination time $t_2$; or each dialysate delivery stroke commencement time $t_1$ is after the respective corresponding dialysate removal stroke commencement time $t_3$ and before the respective corresponding dialysate removal stroke termination time $t_4$.

This arrangement has several advantages over known arrangements. This arrangement may allow for a hybrid of the technical effects of haemodialysis and haemodiafiltration, by allowing for convective operation for part of a pumping cycle. In contrast to known haemodiafiltration, the present arrangement allows for peaks in fluid pressure during part of the pumping cycle, as well as net fluid flow across the dialyser membrane in two directions. This may allow for effective filtration of medium molecular weight molecules without patient fatigue that may result from haemodiafiltration. Repeated peaks in pressure in the dialyser that can result from this method also allow the dialyser membrane to be cleaned, preventing build-up of molecules on the dialyser membrane.

The time between the dialysate delivery stroke commencement time $t_1$ and the dialysate removal stroke commencement time $t_3$ may be a fraction φ of either the dialysate delivery stroke (when $t_3$ is between $t_1$ and $t_2$) or the dialysate removal stroke (when $t_1$ is between $t_3$ and $t_4$), the fraction φ being between 0.01 and 0.99. Preferably, the fraction φ is between 0.05 and 0.95, further preferably the fraction φ is between 0.1 and 0.8. This feature may allow for optimal convective operation.

Each dialysate delivery stroke may be the same duration as its corresponding dialysate removal stroke. The device may be configured such that the first and the second volumes of dialysate are substantially the same. This may facilitate easy fluid monitoring.

The control system may be configured such that the first volume of dialysate is delivered to the dialyser in one inlet pump cycle. The control system may be configured such that the second volume of dialysate is removed from the dialyser in one outlet pump cycle.

The inlet pump assembly may comprise an inlet pump and the outlet pump assembly may comprise an outlet pump, each of the inlet pump and the outlet pump being defined in part by a flexible membrane, the flexible membrane being independently operable between an open position and a closed position for each of the inlet and the outlet pumps. This arrangement may allow for a simple and efficient design of the blood treatment device.

The inlet pump cycle may commence from an inlet pump open position. The outlet pump cycle may commence from an outlet pump closed position.

The dialyser may have an inlet fluidly connected to the dialyser inlet pump and an outlet fluidly connected to the dialyser outlet pump. The inlet pump assembly may comprise a dialyser inlet valve and the outlet pump assembly may comprise a dialyser outlet valve.

The inlet pump and the outlet pump may both be operable to deliver a volume of dialysate from a dialysate source to the dialyser and remove a volume of dialysate from the dialyser. This arrangement may allow for pump-swapping, wherein the inlet pump is operated as an outlet pump, and the outlet pump may operate as an inlet pump. Pump-swapping has the advantage of compensating for any differences in pump size and speeds. For example, even if the inlet pump and the outlet pump are designed to be the same size as each other, manufacturing tolerances may prevent the pumps from being exactly the same size. Such a size difference may result in a flow imbalance over time, which may be corrected for by pump swapping. The control system may be configured to alternate the pump responsible for delivering dialysate to the dialyser and the pump responsible for removing spent dialysate from the dialyser after a given number inlet pump of cycles. The number of inlet pumping cycles may be two or more inlet pumping cycles. Pump-swapping after a minimum of two or more inlet pumping cycles may be an optimal operational mode. The predetermined fraction $\phi$ may be maintained during pump swapping, such that it is the same before and after pump swapping.

The inlet pump and the outlet pump may be arranged to pump a predetermined volume of dialysate.

The inlet pump and the outlet pump may be formed on a disposable cartridge. The dialyser inlet valve and the dialyser outlet valve may be formed on the disposable cartridge. The pumps and valves on the disposable cartridge may be operated by actuation of the flexible membrane by negative and/or positive air pressure.

There may be provided a machine comprising the blood treatment device as defined above. Selective application of the negative/positive air pressure to actuate the pumps and valves on the disposable cartridge may be effected by a pneumatic pump. Each pump or valve may have an associated pneumatic pump on the machine which receives the cartridge. The control system may control the operation of the respective pneumatic pumps. The control system may be a microprocessor which controls the pneumatic pumps electronically. The control may be effected wirelessly.

According to a second aspect of the invention, there is provided a method of operating a blood treatment device, the method comprising the steps of: providing a blood treatment device, the blood treatment device comprising a dialyser, an inlet pump assembly, an outlet pump assembly, and a control system; operating the inlet pump assembly in an inlet pump assembly cycle to deliver a first volume of dialysate from a dialysate source to the dialyser, each inlet pump assembly cycle including a dialysate delivery stroke having a commencement time $t_1$ and a termination time $t_2$; operating the outlet pump assembly in an outlet pump assembly cycle to remove a second volume of dialysate from the dialyser and deliver the second volume of dialysate away from the dialyser, each outlet pump assembly cycle including a dialysate removal stroke having a commencement time $t_3$, wherein for each outlet pump assembly cycle there is a corresponding inlet pump assembly cycle; such that each dialysate removal stroke commencement time $t_3$ is after the respective corresponding dialysate delivery stroke commencement time $t_1$ and before the respective corresponding dialysate delivery stroke termination time $t_2$.

The time between the dialysate delivery stroke commencement time $t_1$ and the dialysate removal stroke commencement time $t_3$ may be a fraction $\phi$ of the dialysate delivery stroke, the fraction $\phi$ being between 0.01 and 0.99. The fraction $\phi$ may be between 0.05 and 0.95. The fraction $\phi$ may be between 0.1 and 0.8. This feature may allow for optimal convective operation.

Each dialysate delivery stroke may be the same duration as its corresponding dialysate removal stroke. The first and the second volumes of dialysate may be substantially the same. This may facilitate easy fluid monitoring.

The first volume of dialysate may be delivered from a dialysate source to the dialyser in one inlet pump cycle. The second volume of dialysate may be removed from the dialyser and delivered away from the dialyser in one outlet pump assembly cycle.

The inlet pump assembly may comprise an inlet pump, and the outlet pump assembly may comprise an outlet pump, each of the inlet pump and outlet pump being defined by a flexible membrane, the membrane being operable between an open position and a closed position for each of the inlet and the outlet pumps. The inlet pump cycle may commence from an inlet pump open position. The outlet pump cycle may commence from an outlet pump closed position. The dialyser may have an inlet fluidly connected to the dialyser inlet pump assembly and an outlet fluidly connected to the dialyser outlet pump assembly. The inlet pump assembly may comprise a dialyser inlet valve and the outlet pump assembly comprises a dialyser outlet valve. The inlet valve and the outlet valve may each be independently operable between an open position and a closed position. Each of the inlet pump and the outlet pump may be defined in part by a flexible membrane, the flexible membrane being independently operable between an open position and a closed position for the inlet and the outlet valves.

The inlet pump assembly and outlet pump assembly may both be operable to deliver a volume of dialysate from a dialysate source to the dialyser and remove a volume of dialysate from the dialyser and deliver said dialysate to the drain.

The method may further comprise the step of alternating the pump responsible for delivering dialysate to the dialyser and the pump responsible for removing spent dialysate from the dialyser after a given number of cycles. The number of pumping cycles may be two or more pumping cycles. This arrangement has the advantages outlined above.

The fraction ϕ may be actively changed depending on dialyser outlet pressure. The fraction ϕ may be controlled by closed loop control. This may reduce the need for manual monitoring of the device.

BRIEF DESCRIPTION OF THE DRAWINGS

Embodiments of the present invention will now be described, by non-limiting example only, with reference to the accompanying drawings, in which.

DESCRIPTION OF EMBODIMENTS OF THE INVENTION

The following detailed description and figures provide examples of how the present invention can be implemented and should not be seen as limiting examples, rather illustrations of how the various features of the convective operation device disclosed herein can be used. Other optional variations will be evident upon a reading of the following description in light of the figures.

Figure 1:
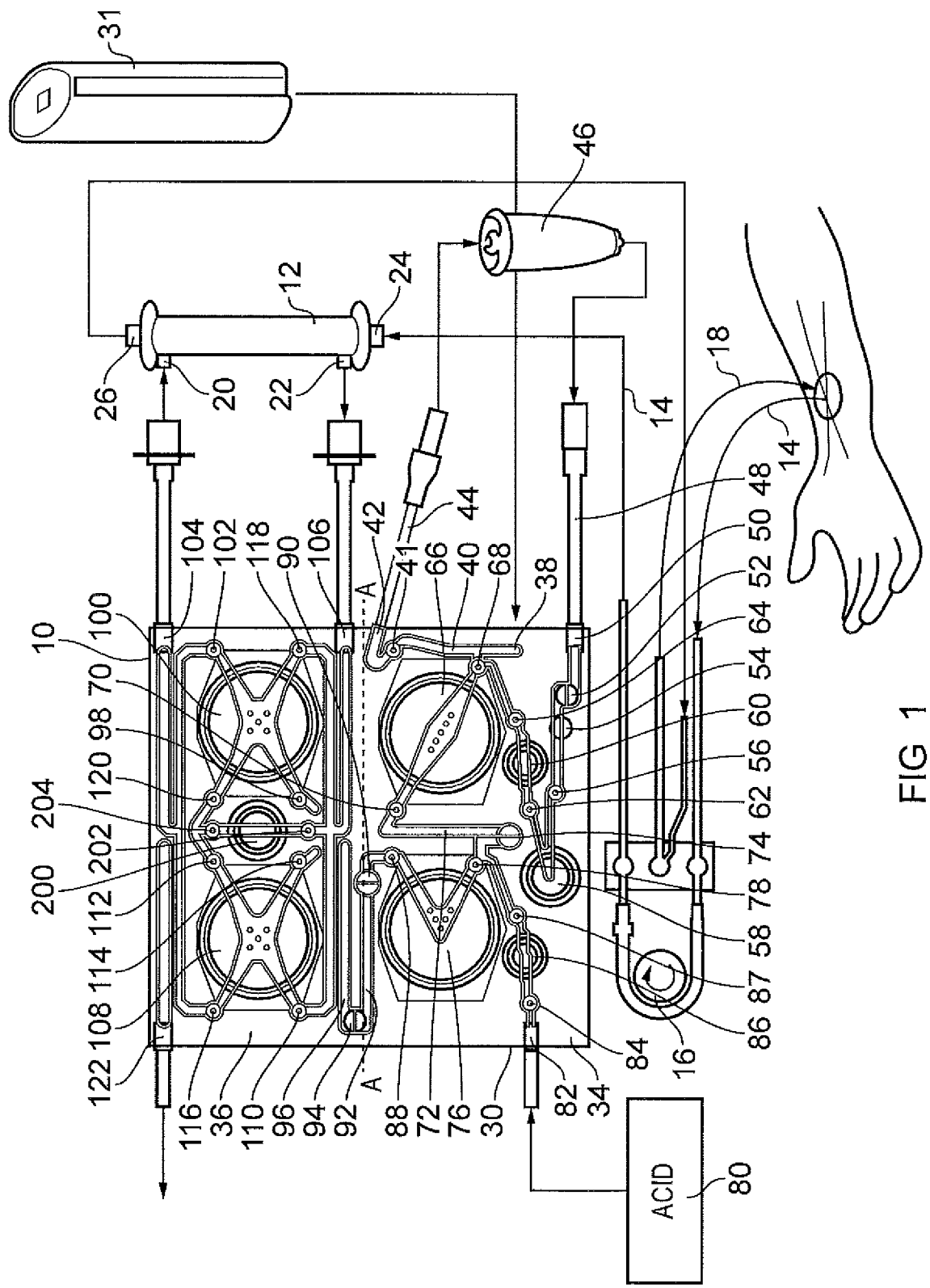
FIG. 1 shows a schematic of a dialysis system having a disposable cartridge comprising a fluid path defined by pumps and valves.
Figure 2:
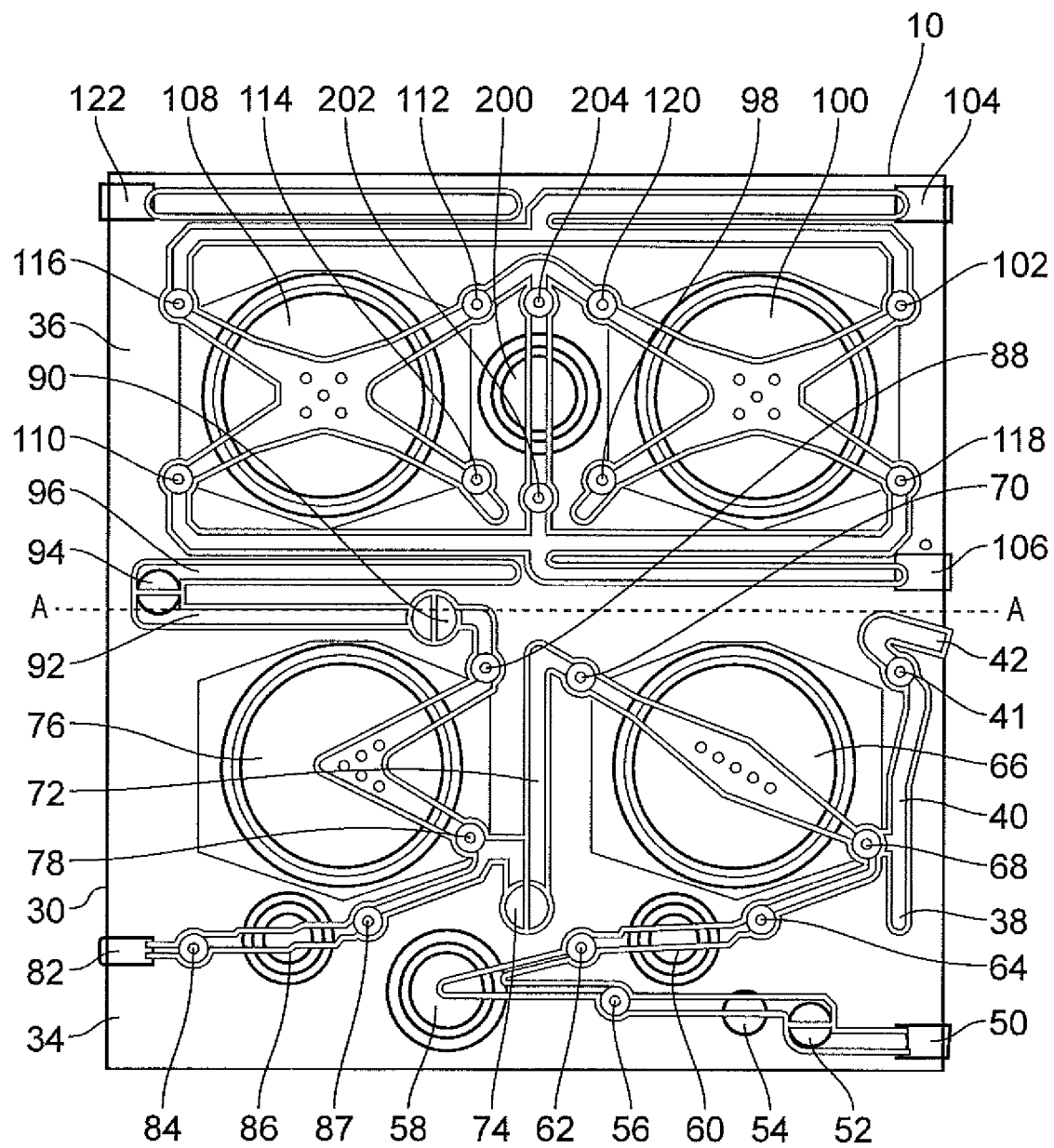
FIG. 2 shows a detailed schematic view of the cartridge of FIG. 1.

Referring to FIGS. 1 and 2, a dialysis system, generally referred to as 10, is shown. A dialyser 12 receives blood via an arterial line 14 connected to a patient by a vascular access device (not shown for clarity), for example a hollow needle as typically used for drawing blood from a patient. The blood is pumped from the patient to the dialyser by a peristaltic pump 16. The blood passes through the dialyser in a known manner and is returned to the patient via a venous line 18. The dialyser 12 comprises a cylindrical tube closed by opposing ends. A semi-permeable membrane (not shown) is provided within the dialyser tube and separates the patient's blood from a dialysate (cleaning) solution. The term "dialysate" used herein does not require that a solution designed to clinical tolerances be used, however a solution designed to within clinical tolerances may be advantageous. The membrane extends substantially between the opposing ends of the cylinder. The dialysate solution removes impurities from the patient's blood in a known manner.

The dialyser has an inlet 20 for receiving clean dialysate solution and an outlet 22 for removing spent dialysate solution from the dialyser 12. The dialyser also has an inlet 24 for receiving untreated blood from the peristaltic pump 16 and an outlet 26 for returning processed blood to the patient. The dialyser 12 is typically provided in a substantially upright orientation, in use, with the patient's blood flowing longitudinally through the dialyser 12 from the blood inlet 24 to the blood outlet 26. The dialysate solution inlet 20 and dialysate solution outlet 22 are configured to be orientated substantially orthogonal to the blood inlet 24 and blood outlet 26, and configured to provide a counter-flow. Dialysate solution is circulated through the hemodialysis machine at a fluid flow rate typically in the range of 500 ml/min to 800 ml/min for approximately four hours.

The dialysis system defines a fluid circuit including a cartridge 30 as will now be described. The cartridge 30 is a consumable component in the hemodialysis machine described.

The cartridge 30 is formed from an acrylic plastic such as SG-10 and has a machine side and a patient side. The cartridge 30 defines pump chambers which are closed by respective diaphragms, formed from, for example, DEHP-free PVC, to define respective pumps. In this embodiment, each diaphragm is part of a single, common sheet of material applied to the machine side of the cartridge 30. The individual diaphragms are operable by pneumatic pressure applied thereto.

A series of flow paths are formed in the cartridge 30 for carrying dialysate solution constituted from water, bicarbonate solution and acid solution. The flow paths are located between the sheet of material closing the machine side of the cartridge 30 and a further sheet of the same material closing the patient side of the cartridge 30.

In use, the variation of pressure applied to the flexible diaphragm of each pump chamber is controlled by conventional valving. A pressure source applies either a positive or negative pressure to one side of the diaphragm of each pump chamber, as required, to pump fluid through the fluid paths in the cartridge 30, in a circuit defined by a plurality of valves.

The valves of the cartridge 30 are conventional diaphragm valves defined by respective openings in the cartridge 30 and closed by respective flexible diaphragms. Each valve is operable by applying a negative pressure to the diaphragm to open the valve and applying a positive pressure to the diaphragm to close the valve. The diaphragm of each valve is part of the single, common sheet of material applied to the machine side of the cartridge 30. The valves are opened and closed according to a flow control strategy, as will become apparent.

The machine side of the cartridge 30 abuts a pump driver (not shown) comprising a platen having a plurality of recessed surfaces, each recessed surface substantially corresponding in geometry and volume to a pump chamber defined in the cartridge 30. Each recessed surface has a fluid port connectable with a source of positive fluid, typically, pressure and, with a source of negative fluid pressure via a valve.

Figure 4:
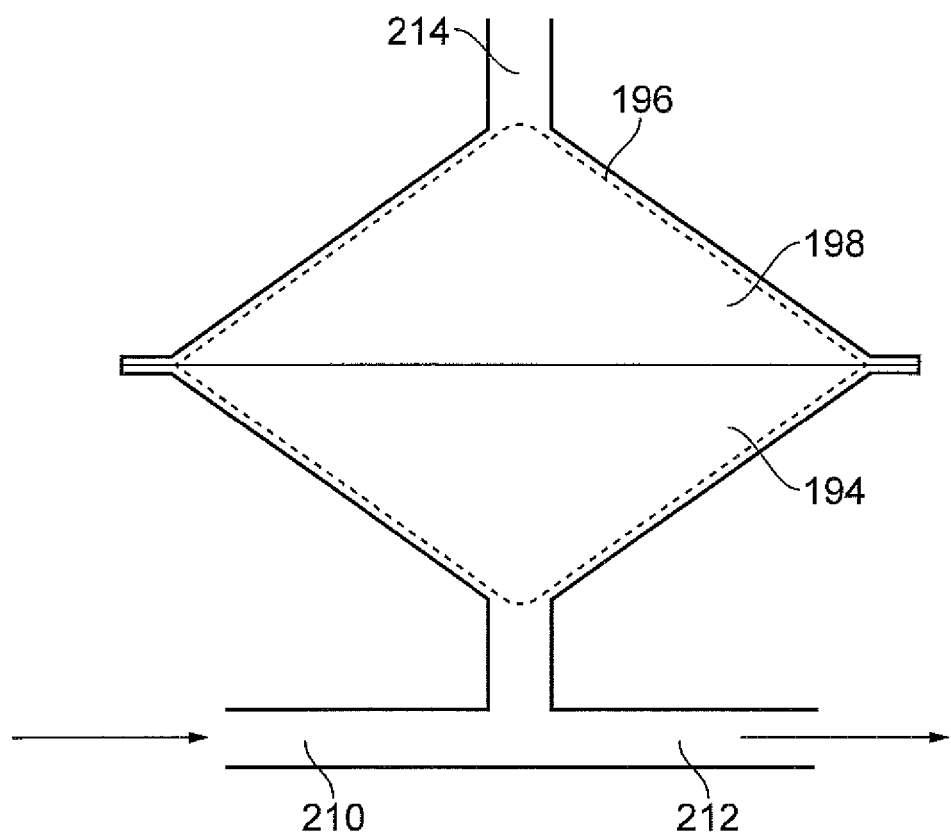
FIG. 4 shows a schematic cross-section through a pump of the type defined by the disposable cartridge.

A cartridge fluid pump and corresponding platen chamber are shown in FIG. 4. The positive and negative fluid pressure sources include a pressure pump and a vacuum pump respectively. When the valve is operated to allow fluid to flow into a recessed surface from the source of positive fluid pressure, the diaphragm moves into a corresponding pump chamber and any fluid, i.e. dialysate solution, therein is expelled from that pump chamber via the series of flow paths. When the valve is operated to allow fluid to flow out of a recessed surface to the source of negative fluid pressure, the diaphragm is moved away from a pump chamber and into the corresponding recessed surface to permit fluid to be drawn into that pump chamber via the series of flow paths. The surface of the pump chambers and of the platen provide a positive stop for each diaphragm, to prevent overstretching thereof. The positive stop ensures that the volume of fluid drawn into and pumped from the pump chambers is accurately controlled.

The cartridge 30 has two main functions, preparation of dialysate solution and flow balance. Each function is performed by a separate part of the cartridge as illustrated in FIGS. 1 and 2 by the schematic separation of the cartridge into two parts by the line A-A in the figures. The dialysate preparation function is performed by one part of the cartridge, generally referred to at 34 and the flow balance function is performed by the other part of the cartridge, generally referred to at 36. The cartridge 30 prepares an accurately mixed homogenous dialysate solution and ensures that the flow of clean dialysate supplied to the dialyser 12 matches (to within clinical tolerances) the volume of spent dialysate drawn from the dialyser 12.

The cartridge 30 is provided with a plurality of connections to and from the cartridge 30 as described below. A first inlet port 38, from hereon referred to as the water inlet port, defined in the machine side of the cartridge 30 receives purified water from a purified water supply 31 such as a reverse osmosis water supply.

A first outlet port 42, from hereon referred to as the water outlet port, defined in an edge of the cartridge 30 directs the purified water to a first dialysate solution constituent which, in the illustrated embodiment shown in FIGS. 1 and 2, is bicarbonate 46.

A second inlet port 50, from hereon referred to as the bicarbonate inlet port, defined in the same edge of the cartridge 30 as the water outlet port 42 receives purified water mixed with the bicarbonate 46.

A third inlet port 82, from hereon referred to as the acid inlet port, defined in the opposite edge of the cartridge 30 to the water outlet port 42 and bicarbonate inlet port 50 receives a second dialysate solution constituent which, in the illustrated embodiment shown in FIGS. 1 and 2, is acid 80.

A second outlet port 104, from hereon referred to as the clean dialysate solution outlet port, is defined in the same edge of the cartridge as the water outlet port 42 and the bicarbonate inlet port 50. The clean dialysate outlet port 104 directs clean dialysate solution to the dialyser 12.

A fourth inlet port 106, from hereon referred to as the spent dialysate solution inlet port, is defined in the same edge of the cartridge 30 as the water outlet port 42, bicarbonate inlet port 50 and clean dialysate outlet port 104. The spent dialysate solution inlet port 106 receives spent dialysate solution from the dialyser 12.

A third outlet port 122, from hereon referred to as the drain port, is defined in the same edge of the cartridge as the acid inlet port 82. The drain port 122 directs spent dialysate solution out of the cartridge 30.

Operation of the Device

Figure 3:
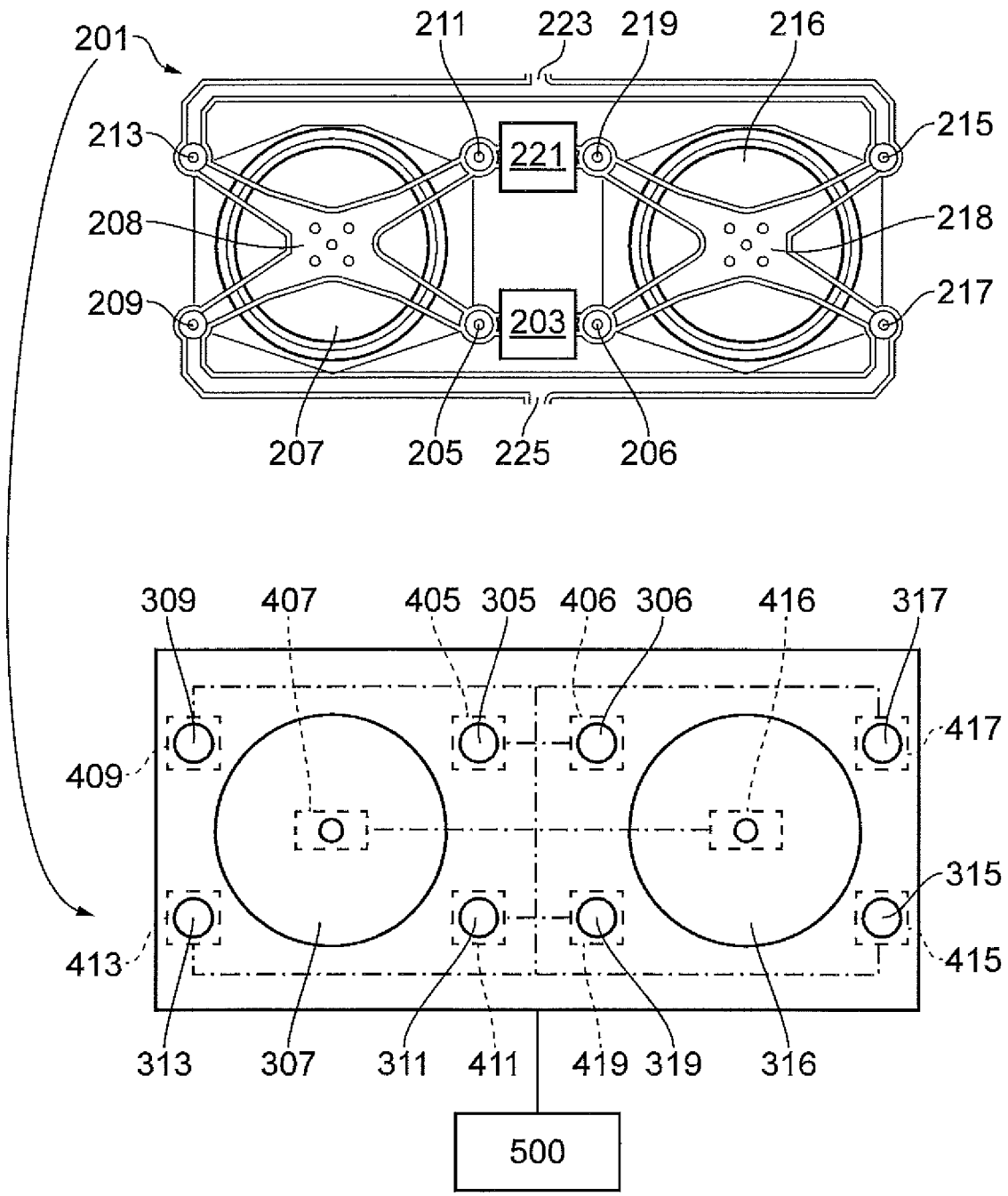
FIG. 3 shows a schematic representation of a pump and valve arrangement.

FIG. 3 shows a schematic representation of the pump and valve arrangement 201 of the invention. In this case, the pump and valve arrangement 201 is provided by the combination of a membrane pump cartridge (or part cartridge) and a vacuum pump array with platen. The membrane pump cartridge is similar in layout to the flow balance pump arrangement described above.

The membrane pump cartridge comprises first and second source valves 205, 206, first and second pumps 207, 216 and first and second pump chambers 208, 218, first and second dialyser inlet valves 209, 217 and first and second dialyser outlet valves 213, 215.

The vacuum pump array and platen comprises a platen having a pattern of circular depressions which correspond in position and size to the valves and pumps on the pump cartridge. In the figure, these are numbered 100 higher than the membrane pump features.

Each depression has an aperture at the base thereof which is in fluid communication with an associated vacuum pump. Each vacuum pump, shown in broken lines as they sit on the rear face of the platen, is numbered 100 higher than the respective associated platen feature.

All of the vacuum pumps are connected to a control system 500. The control system 500 is a microprocessor which operates the vacuum pumps 405-419 in a manner so as to effect either convective operation or haemodialysis as described below. The connection to the pumps may be wired or wireless. Wireless connection options include IR, Bluetooth or WIFI, amongst others.

The dialysate is produced elsewhere on the cartridge by mixing acid and bicarbonate compounds with a set volume of water provided by a reverse osmosis machine which has been sterilised. This forms the source of dialysate 327 used by the pump and valve arrangement 201.

All valves and pumps are independently operable. In one embodiment, all pumps 207, 216 and all valves 205, 206, 211, 209, 213, 215, 217, 219 are independently operable by pneumatic pressure applied to the flexible membrane.

By selectively operating the vacuum pumps, the control system controls the opening and closure of the valves as well as actuation of the first and second pumps. The microprocessor control system is programmable to operate the valves in a variety of different configurations. Based on the programming of the controller, the controller will communicate with each of the valves or means for operating the valves, so that each valve may be opened and closed independently based on the programming entered into the controller by the user, skilled operator or programme instructions.

The apparatus described can be used in different modes: simple haemodialysis mode and phased convective operation mode. The device described above is adapted such that each mode can be actively controlled. Such control can prevent accidental use of the wrong mode at any given time, and allow tailoring of the convective operation method.

Cartridge Cleaning

After each use, the hemodialysis machine requires sanitising to prevent contamination of a patient's bloodstream during subsequent dialysis sittings. The removable cartridge 30, as described above, is usually disposed of after each sitting. In one embodiment of the invention, the cartridge 30 is sanitised to allow re-use in subsequent dialysis sittings. Such sanitisation may include steps of operating the device as it would be used during haemodialysis or convective operation. In one sanitisation method, dialysate may be caused to flow through the device in the same way or a similar way to how dialysate would flow during haemodialysis, haemodiafiltration or phased convective operation.

Haemodialysis Mode

The pumping cycle of the first mode of operation of the arrangement 201 begins with closure of the first and second dialyser inlet valves 209, 217 and the first and second dialyser outlet valves 213, 215. The first source valve 205 and the first drain valve 219 are opened, the second source valve 206 and second drain valve 211 are closed. The first pump 207 is then operated to draw dialysate 327 from the dialysate source 203 into the first pump chamber 208 of the first pump 207 and the second pump 216 is operates to expel dialysate 327 within the second pump chamber 218 of the second pump 216 into the drain 221. Accordingly, the dialysate 327 in the dialysate source 203 is drawn into the first pump chamber 208 by the negative pressure created as the membrane of the first pump chamber 208 is drawn away from the pump chamber by vacuum means in the dialysis machine (not shown). The dialysate 327 in the second pump chamber 218 is subjected to a positive pressure as the membrane in the second pump 216 is forced into the second pump chamber 218 thus driving the dialysate out through the open first drain valve 219 to be discarded.

In the next stage of the pump cycle, the first dialyser inlet valve 209 and the first dialyser outlet valve 215 are opened and the first source valve 205 and the first drain valve 219 are closed. The first pump 207 is then actuated to expel the dialysate 327 from within the first pump chamber 208 into the dialyser (not shown) and the second pump 216 is actuated to pull spent dialysate 327 from the dialyser (not shown) into the second pump chamber 218. In this step, the dialysate 327 in the first pump chamber 208 has a positive pressure applied to it as the membrane is forced down into the first pump chamber 208 thereby forcing the dialysate 327 through the dialysis circuit and into the dialyser. In the dialyser, dialysate 327 is passed in a typically counterflow arrangement to the blood of the patient and waste products diffuse across the dialyser membrane into the dialysate 327 via diffusion. The movement of the dialysate 327 through the dialyser and into the second pump chamber is assisted by a negative pressure generated by the membrane of the second pump chamber which is retracted by the vacuum means on the dialysis machine, operated by the device's controller. These two stages are repeated and then, in the third stage of the pump cycle, the first dialyser inlet valve 209 and first dialyser outlet valve 215 are closed, the first drain valve 219 is opened and second pump 216 actuated to expel the spent dialysate 327 from the second pump chamber 218 into the drain 221. Accordingly, after the completion of this step, both pump chambers 208, 218 are empty.

In the fourth step of the cycle, the first drain valve 219 is closed and the second source valve 206 is opened in order to allow the second pump 216 to draw dialysate from the source 203 into the second pump chamber 218. In the fifth step, with the second pump chamber 218 now filled, the second dialyser inlet valve 217 the second dialyser outlet valves 213 are opened and the second source valve is closed. The second pump 216 is actuated to expel the dialysate in the second pump chamber 218 into the dialyser (not shown) and the first pump 207 is actuated to draw dialysate from the dialyser into the first pump chamber 208. This allows the same operation as was carried out in the first and second steps to proceed but with the roles of the pumps 207, 216 swapped around. Thus any small discrepancies between the volumes of the two pump chambers 208, 218 are cancelled out.

The fourth and fifth steps are repeated and finally, the second dialyser outlet valve 213 and second dialyser inlet valve 217 are closed, the second drain valve 211 and second source valves are opened and the first pump 207 is operated to expel the dialysate from the first pump chamber 208 into the drain 221.

Phased Convective Operation Mode

In contrast to the haemodialysis mode described above, phased convective operation does not operate with pump movements that are directly synchronised with each other.

There are two main ways in which phased convective operation can be achieved. In the first, referred to herein as "phase-delay convective operation" mode, each dialysate removal stroke commencement time $t_3$ is after the respective corresponding dialysate delivery stroke commencement time $t_1$ and before the respective corresponding dialysate delivery stroke termination time $t_2$. Phase-delay convective operation is analogous to (but not the same as) pre-dilution in haemodiafiltration. In the second, referred to herein as "phase-advance convective operation" mode, each dialysate delivery stroke commencement time $t_1$ is after the respective corresponding dialysate removal stroke commencement time $t_3$ and before the respective corresponding dialysate removal stroke termination time $t_4$. Phase-advance convective operation is analogous to (but not the same as) post-dilution in haemodiafiltration.

For simplicity, phase-delay convective operation (that is analogous to pre-dilution in haemodiafiltration) will be described in detail. It should be understood that the second option will have a corresponding technical effect as the first option. The second option will be described briefly with reference to FIG. 7.

One aim of phased convective operation is to achieve peaks in pressure in the dialyser, so that convective operation occurs repeatedly but for short amounts of time (i.e. not during a whole pump action).

Phase-delay convective operation achieves this by blocking or inhibiting fluid from leaving an outlet 22 of the dialyser 12, while fluid is being caused to flow through the dialyser inlet 20. As fluid continues to flow through the inlet 20, the outlet 22 is opened.

The time difference between fluid commencing flow through the inlet 20 and fluid commencing flow through the outlet 22 is controlled, such that the dialysate delivery stroke commencement time and the dialysate removal stroke commencement time are always separated by a time delay $\delta t$.

It should be understood that the equations below represent an example of how the pump assemblies can be operated to produce the required phase delay. It should be understood that the pump assemblies can be operated in a variety of different ways to achieve the required phase delay effects.

Each inlet pump delivery stroke (and by definition inlet pump cycle) commences at time $t_1 = t_a + x\, t_{ip}$, each outlet pump cycle commences at a time $t_3 = t_a + x\, t_{op}$, wherein $t_a$ is the commencement time of the first inlet pump cycle, $t_b$ is the commencement time of the first outlet pump cycle, x is an integer corresponding to the number of pump cycles, $t_{ip}$ is the time for each full inlet pump cycle, and $t_{op}$ is the time for each full outlet pump cycle.

In phase-delay convective operation, the time delay $\delta t$ is governed by a pre-determined fraction $\phi$ of the delivery stroke time $(t_2 - t_1)$, where:

$$\delta t = \phi(t_2 - t_1)$$

wherein $t_2$ is the delivery stroke termination time.

The pre-determined fraction $\phi$ may also govern the delay $\delta t$ between the delivery stroke termination time $t_2$ and the removal stroke termination time. This causes a pressure drop in the dialysate side of the dialyser 12, such that dialysate and dissolved medium molecular weight waste particles can be dragged back across the dialyser semi-permeable membrane and be removed.

The time delay $\delta t$ between delivery stroke commencement time and the removal stroke commencement time may equally be different to the time delay between the delivery stroke termination time and the removal stroke commencement time.

Comparison of Haemodialysis and Phase-Delay Convective Operation

Figure 5:
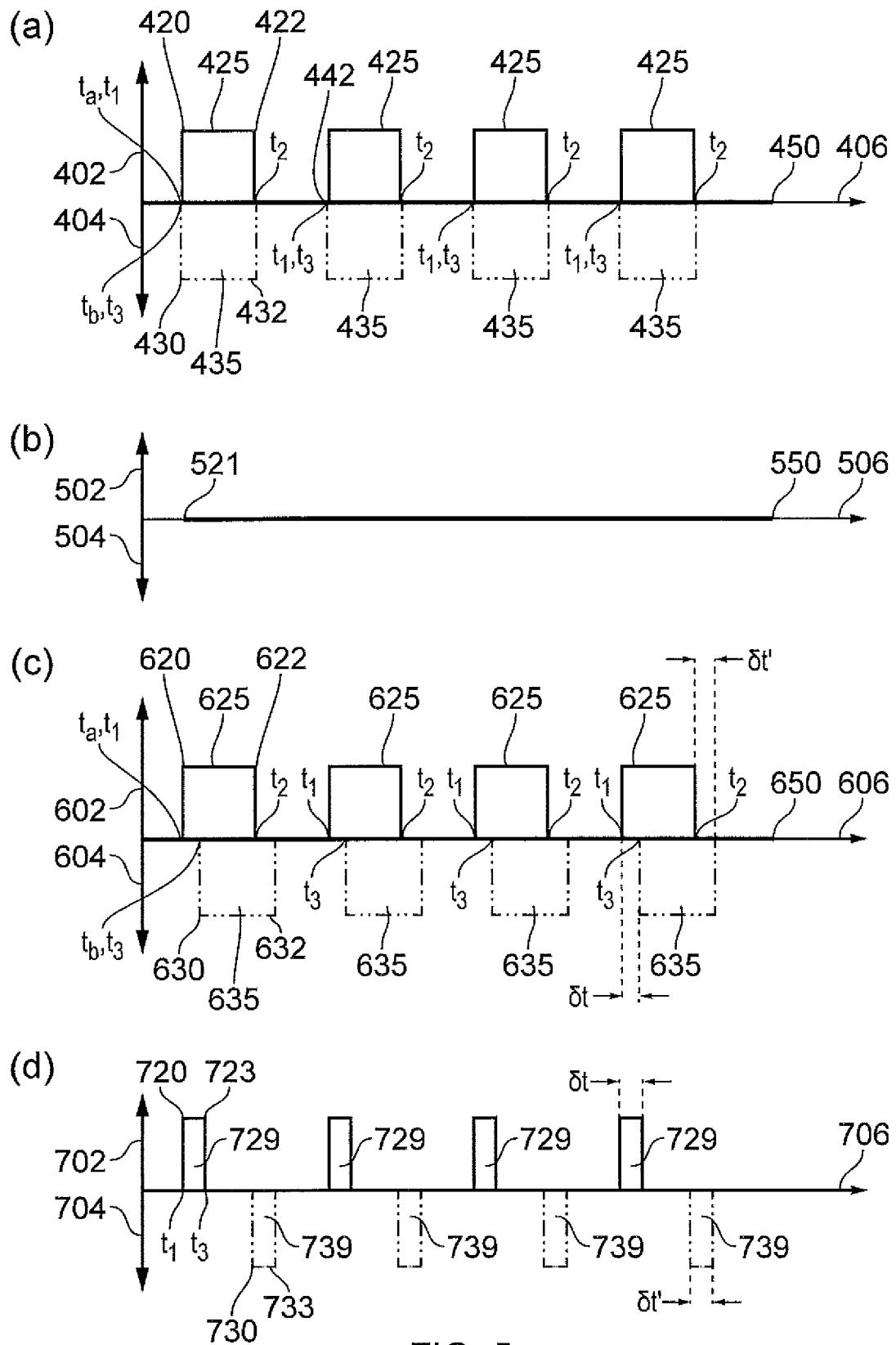
FIG. 5 shows an idealised schematic of the pressure in the dialyser for (a) normal haemodialysis (inlet/outlet); (b) net haemodialysis; (c) phase-delay convective operation (inlet/outlet); (d) net phase-delay convective operation.

FIGS. 5*a* to 5*d* are idealised depictions which demonstrate the function of the phase-delay method (FIGS. 5*c* and 5*d*) in contrast to a haemodialysis method (FIGS. 5*a* and 5*b*). Real measurements would differ from these due to various factors, including but not limited to: fluid inertia, drag, dimensional differences, or pulsatile blood pressure changes. FIG. 5 is an idealised depiction of pressure over time for (a) normal haemodialysis (inlet/outlet); (b) net pressure in haemodialysis; (c) phase-delay convective operation (inlet/outlet); and (d) net pressure in phase-delay convective operation.

FIG. 5*a* shows the inlet pressure (solid line) and the outlet pressure (dashed line) of idealised haemodialysis on a graph having axes of inlet pressure 402, and outlet pressure 404 against time 406. This may correlate directly to inlet flow rate and outlet flow rate, which in practice can be measured at the required inlet 20 and outlet 22 flow paths of the dialyser 12. The square-shaped peaks in the solid line are due to the pulsatile pump cycles of the inlet pump 207. The square-shaped peaks in the dashed line may be due to forced fluid from the inlet pump 207, pulsatile synchronised opening and closing of an outlet valve 213, or synchronised opening and closing of an outlet pump 216.

Time point $t_1$ to time point $t_2$ denotes one inlet pump assembly dialysate delivery stroke. Time point $t_1$ to the following time point $t_1$ denotes one inlet pump cycle.

In FIG. 5*a* (which shows haemodialysis only), time point $t_3$ to time point $t_2$ denotes one outlet pump assembly dialysate removal stroke. Time point $t_3$ to the following time point $t_3$ denotes one outlet pump cycle.

At time point $t_1$ of FIG. 5*a*, the inlet pump 207, which is full of dialysate, is actuated, by actuating the membrane of the inlet pump downwards, to force the dialysate into the dialyser 12. The inlet pump 207 continues to do this until point 422 (corresponding time point $t_2$), at which time it has been fully actuated and there is no dialysate in the inlet pump 207 to force through to the dialyser. At this point the membrane of the inlet pump 207 will contact the bottom of the inlet pump 207.

At time point $t_3$ of FIG. 5*a* (equivalent in haemodialysis to $t_1$), the outlet pump 216, which is empty of dialysate, is actuated, by actuating the membrane of the outlet pump 216 upwards, to force the dialysate out of the dialyser 12 and into the outlet pump 216. The outlet pump 216 continues to do this until point 422, at which time it has been fully actuated and there is no more room in the outlet pump 216 to accommodate further dialysate. At this time the membrane of the outlet pump 216 will contact the top of the outlet pump 216.

From point $t_2$ to point $t_1$, the inlet pump 207 is actuated to draw dialysate from a source into the inlet pump 207. No dialysate is caused to flow into the dialyser 12 during this time. This may be by means of actuation of a valve to close an inlet to the dialyser 12. From point $t_2$ to $t_1$, the outlet pump 216 is actuated to force dialysate from the outlet pump 216 to a location away from the dialyser 12, which may be a drain or another part of the machine circuit. No dialysate is caused to flow out of the dialyser 12 during this time. This may be by means of actuation of a valve to close an outlet to the dialyser 12.

The inlet pressure line in FIG. 5*a* has four square-shaped peaks 425. The four square-shaped peaks 425 are equally sized, shaped, and spaced. The four peaks 425 represent a sample of idealised inlet pressure changes during haemodialysis. The first peak starts at point $t_a$, where it instantaneously increases to a pressure 420. It stays at this pressure until point 422 at which time it instantaneously decreases to zero. It stays at zero until time 442, at which time the second peak occurs and it increases to a pressure equal to that of the first peak, pressure 420.

The outlet pressure line in FIG. 5*a* also has four square-shaped peaks 435. The term "peaks" has been used as the axis 404 is a positive axis, and is only denoted below the inlet pressure axis for easy comparison. The four square-shaped peaks 435 are equally sized, shaped, and spaced. The four peaks 435 represent a sample of idealised inlet pressure changes during haemodialysis. The first peak starts at point $t_b$, where it instantaneously increases to a pressure 430. It stays at this pressure until point 432 at which time it instantaneously decreases to zero. It stays at zero until time 442, at which time the second peak occurs and it increases to a pressure equal to that of the first peak, pressure 430.

As shown by FIG. 5*a*, in an idealised depiction of haemodialysis, the inlet and outlet pressure traces exactly mirror each other. These traces reflect the inlet and outlet pump cycles of the blood treatment device.

The solid line can be represented with the function described above, wherein:

Each inlet pump delivery stroke (and by definition inlet pump cycle) commences at a time $t_1$;

$$t_1(x) = t_a + x\, t_{ip},$$

The dashed line can also be represented with the function described above, wherein:

Each outlet pump cycle commences at a time $t_3$;

$$t_3(x) = t_b + x\, t_{op},$$

and wherein $t_a$ is the commencement time of the first inlet pump cycle, $t_b$ is the commencement time of the first outlet pump cycle, and x is an integer corresponding to the number of pump cycles.

In haemodialysis, there is no delay between $t_1$ and $t_3$.

Considering the delay function:

$$\delta t = \phi(t_2 - t_1)$$

wherein $t_2$ is the delivery stroke termination time.

The pre-determined fraction in haemodialysis must be zero. In haemodialysis, there is no pre-determined fraction $\phi$, and no resulting net peaks in pressure.

As shown in FIG. 5*b*, in an idealised depiction, there is no net pressure change in the dialyser during haemodialysis. The graph in FIG. 5*b* has an axis representing overall pressure in the dialyser and a time axis 506. The overall pressure axis has a positive section 502 and a negative section 504. A net result of zero magnitude from time 521 to 550 is shown along the time axis 506, corresponding to the starting and finishing points of the sample shown in FIG. 5*a*. This zero net result is because, as shown in idealised FIG. 5*a*, the inlet pressure exactly matches the outlet pressure for haemodialysis. FIG. 5*c* shows the inlet pressure (solid line) and the outlet pressure (dashed line) of phase-delay convective operation.

FIG. 5*c* shows the inlet pressure (solid line) and the outlet pressure (dashed line) of idealised phase-delay convective operation on a graph having axes of inlet pressure 602, and outlet pressure 604 against time 606. This may correlate directly to inlet flow rate and outlet flow rate, which in practice can be measured. The square-shaped peaks 625 in the solid line are due to the pulsatile pump cycles of the inlet pump 207. The square-shaped peaks 635 in the dashed line may be due to pulsatile opening and closing of an outlet valve 213, or opening and closing of an outlet pump 216.

The inlet pressure line in FIG. 5c has four square-shaped peaks 625. The four square-shaped peaks 625 are equally sized, shaped, and spaced. The four peaks 625 represent a sample of idealised inlet pressure changes during phase-delay convective operation. The first peak starts at time point $t_a$, where it instantaneously increases to a pressure 620. It stays at this pressure until point 622 at which time it instantaneously decreases to zero, at time point $t_2$. It stays at zero until the following time $t_1$, at which time the second peak occurs and it increases to a pressure equal to that of the first peak, pressure 620.

At point $t_1$ of FIG. 5c, the inlet pump 207, which is full of dialysate, is actuated, by actuating the membrane of the inlet pump downwards, to force the dialysate into the dialyser. The inlet pump 207 continues to do this until point 622, at which time it has been fully actuated and there is no dialysate in the inlet pump 207 to force through to the dialyser. At this time the membrane of the inlet pump 207 will contact the bottom of the inlet pump 207. From point $t_2$ to point $t_1$, the inlet pump 207 is actuated to draw dialysate from a source into the inlet pump 207. No dialysate is caused to flow into the dialyser 12 during this time. This may be by means of actuation of a valve to close an inlet to the dialyser 12. This sequence of events (from point $t_a$ to following point $t_1$) represents one inlet pump cycle.

At point $t_3$ of FIG. 5c, the outlet pump 216, which is empty of dialysate, is actuated, by actuating the membrane of the outlet pump 216 upwards, to force the dialysate out of the dialyser 12 and into the outlet pump 216. The outlet pump 216 continues to do this until point 632, at which time it has been fully actuated and there is no more room in the outlet pump 216 to accommodate further dialysate. At this point the membrane of the outlet pump 216 will contact the top of the outlet pump 216. From point 632 to the following $t_3$, the outlet pump 216 is actuated to force dialysate from the outlet pump 216 to a location away from the dialyser 12, which may be a drain or another part of the machine circuit. No dialysate is caused to flow out of the dialyser 12 during this time, which may be by means of actuation of a valve to close an outlet to the dialyser 12. This sequence of events (from point $t_b$ to following point $t_3$) represents one outlet pump cycle.

The outlet pressure line in FIG. 5c also has four square-shaped peaks 635. The term "peaks" has been used as the axis 604 is a positive axis, and is only denoted below the inlet pressure axis for easy comparison. The four square-shaped peaks 635 are equally sized, shaped, and spaced relative to each other. The four peaks 635 represent a sample of idealised outlet pressure changes during phase-delay convective operation. The first peak starts at point $t_3$, where it instantaneously increases to a pressure 630. It stays at this pressure until point 632 at which time it instantaneously decreases to zero. It stays at zero until the following time $t_3$, at which time the second peak occurs and it increases to a pressure equal to that of the first peak, pressure 630.

In contrast to haemodialysis illustrated in FIG. 5a, the inlet and outlet traces in phase-delay convective operation (FIG. 5c) are offset relative to each other. In particular, the outlet pressure peaks occur after the inlet pressure peaks by an amount δt. The outlet pressure peaks also terminate after the inlet pressure peaks by an amount δt. The net pressure peaks are shown by FIG. 5c.

Similar to haemodialysis, the solid line can represented with the function described above, wherein:

Each inlet pump delivery stroke (and inlet pump cycle) commences at a time $t_1$;

$$t_1(x)=t_a+x\, t_{ip},$$

The dashed line can also be represented with the function described above, wherein:

Each outlet pump removal stroke (and outlet pump cycle) commences at a time $t_3$;

$$t_3(x)=t_b+x\, t_{op},$$

and wherein $t_a$ is the commencement time of the first inlet pump cycle, $t_b$ is the commencement time of the first outlet pump cycle, and x is an integer.

With phase-delay convective operation there is a delay between $t_1$ and corresponding $t_3$.

Considering the delay function:

$$\delta t=\phi(t_2-t_1)$$

wherein $t_2$ is the delivery stroke termination time.

The pre-determined fraction in phase-delay convective operation is a number between 0 and 1. In phase-delay convective operation, there is a pre-determined fraction φ, and net peaks in pressure, as shown in FIG. 5d.

FIG. 5d represents the idealised net pressure in the dialyser during phase-delay convective operation. As shown in FIG. 5d, there are net pressure changes in the dialyser during convective operation. The graph in FIG. 5d has an overall pressure in the dialyser axis, the overall pressure axis having a positive section 702, a negative section 704 and a time axis 706. The four rectangular peaks in net pressure 729 correspond to the times when the inlet pressure peaks and the outlet pressure is zero. The first peak starts at time $t_1$ and peaks to point 720, and finishes at time $t_3$ (corresponding point 723). Each peak 729 lasts for time δt. The four rectangular troughs in net pressure 739 correspond to the times when the outlet pressure "peaks" (a trough relative to dialyser pressure) and the inlet pressure is zero. The first trough 739 starts at time 730 and finishes at time 733, lasting for time δt'. Each trough lasts for time δt'. It is not necessary for the commencement time delay δt to be the same as the termination delay δt' as shown later with FIG. 8, however this may be advantageous.

Any net pressure (peak or trough) corresponds to a driving pressure in the dialyser, which can force particles across the semi-permeable membrane in the dialyser. A net pressure peak results in dialysate being forced across the semi-permeable membrane from the dialysate side to the blood side of the dialyser. This forcing may clear the membrane of particles which may build up on the membrane. A net trough in pressure results in dialysate being dragged across the semi-permeable membrane from the blood side to the dialysate side of the dialyser. The dialysate being dragged back across the semi-permeable membrane will drag with it medium molecular weight waste molecules.

As outlined above with reference to FIGS. 5a to 5d, in contrast to pump operation during convective operation, during phase-delay convective operation, pump operation is not directly synchronised. The inlet pump assembly may be forcing fluid into the dialyser before the outlet pump assembly starts to allow fluid out of the dialyser. Equally, the inlet pump assembly may finish forcing fluid into the dialyser 12 before the outlet pump assembly finishes allowing fluid removal from the dialyser 12.

Worked Example

Figure 6:
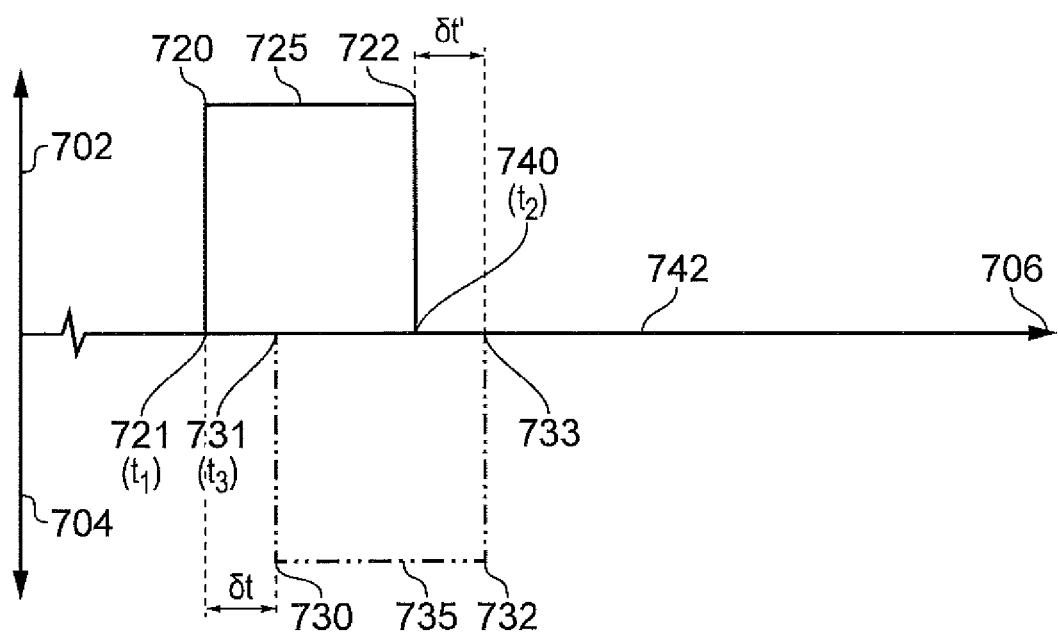
FIG. 6 is an enlarged view of the fourth pump cycles of the inlet and outlet pumps of the phase-delay convective operation graph in FIG. 5c.

FIG. 6 shows an enlarged view of the fourth pump cycles of the inlet and outlet pumps of the phase-delay convective operation graph in FIG. 5c.

As described previously, idealised phase-delay convective operation is plotted on a graph having axes of inlet pressure 702, and outlet pressure 704 against time 706. This may correlate directly to inlet flow rate and outlet flow rate, which in practice can be measured. The square-shaped peak 725 in the solid line is due to the fourth pulsatile pump cycle of the inlet pump, in particular due to an inlet pump delivery stroke. The square-shaped peak 735 in the dashed line is due to the fourth outlet pump removal stroke, which may be due to pulsatile opening and closing of an outlet valve 213, or opening and closing of an outlet pump.

This worked example considers the time factors of the outlet pump when the inlet pump time factors are known, and when the pre-determined fraction is known.

As an example, the first pump cycle of the inlet pump 207 ($t_a$) starts after 1 second, i.e. $t_a=1$. Also by way of example, each inlet pump cycle takes two seconds (one second to draw fluid in from a source, and one second to force fluid out to a drain or circuit).

Given that:

$$t_1 = t_a + x \, t_{ip},$$

And given that for this example, $$t_1 = 1 + 2x$$

For the fourth pump cycle (shown in FIG. 6), x=4. So:

$$t_1 = 1 + 2*4$$

$$t_1 = 9 \text{ seconds}$$

Therefore point 721 ($t_1$) of FIG. 6 corresponds to 9 seconds from the method start time. Point 740 ($t_2$) of FIG. 5 corresponds to 10 seconds and point 742 of FIG. 6 corresponds to 11 seconds.

As stated above, the delay function is:

$$\delta t = \phi(t_2 - t_1)$$

Accordingly:

$$\delta t_{=1\phi}$$

In this worked example, φ is set at 0.2, however as stated previously, various possible values of φ are possible.

This gives a delay function value of:

$$\delta t = 1*0.2$$

$$\delta t_{=0.2}$$

Point 731 ($t_3$) of FIG. 6 (start of fourth outlet pump cycle and start of fourth outlet pump delivery stroke), as shown by FIG. 6, is δt seconds after point 721. Point 731 ($t_3$, start of fourth inlet pump cycle) is therefore at 9.2 seconds, point 733 (midpoint of fourth inlet pump cycle) is at 10.2 seconds and point 742 (end of fourth inlet pump cycle) is at 11.2 seconds.

Finding point 731 ($t_3$) using the outlet pump cycle time function gives the same result:

$$t_3 = t_b + x \, t_{op},$$

$$t_3 = (t_a + \delta t) + x \, t_{op}$$

$$t_3 = (1 + 0.2) + 4*2$$

$$t_3 = 9.2$$

During the 0.2 seconds at the start of the first pump cycle (point 721 ($t_1$) to 731 ($t_3$)), the pressure in the dialyser is peaked. In theory, in the idealised example given, dialysate will transfer from the dialysate side of the dialyser to the blood side of the dialyser in this first 0.2 seconds. In the following 0.8 seconds of the first pump cycle (point 731 ($t_3$) to 740 ($t_2$)), there is no net transfer of fluid across the semi-permeable membrane of the dialyser. In the following 0.2 seconds (point 740 ($t_2$) to 733), dialysate will transfer from the blood side of the dialyser to the dialysate side of the dialyser. For the following 0.8 seconds of the first pump cycle (point 733 to 742), there is no net transfer of fluid across the semi-permeable membrane of the dialyser.

As shown by the worked example given above (which is given as an example of what the functions represent and should not be seen as limiting values), a key factor in the relation between the inlet pump cycle and the outlet pump cycle is the pre-determined fraction φ.

The pre-determined fraction φ can be actively caused to change during the course of the method. For example, the pre-determined fraction φ could be set at a certain value for a first number of pump cycles, and set at a different value for a second number of pump cycles. Equally, as mentioned above, the device could be operated in a haemodialysis mode for a first number of pump cycles, and operated in a phase-delay convective operation method or a phase-advance convective operation method for a second number of pump cycles. The device could equally be operated in a conventional haemodiafiltration mode for a first number of pump cycles, and in a phase-delay convective operation method or a phase-advance convective operation method for a second number of pump cycles. Any sequence or combination of haemodialysis, phase-delay convective operation, phase-advance convective operation, or conventional haemodiafiltration may be possible.

Control of the operating method of the device may be through a closed loop control. A sensor, such as a pressure sensor, may be used to measure the pressure of the fluid at the outlet of the blood side of the dialyser. This may be indicative of the amount of fluid being removed from the blood at any given time, and may give an indication of haematocrit. This information can be used to control the pre-determined fraction φ during phased convective operation, or to change the method of operation of the device, for example to a haemodialysis mode. For example, if an indication that haematocrit level is too high, for example because too much fluid has been removed from the blood, then the device could reduce the pre-determined fraction φ, or change the pre-determined fraction φ to 0 such that haemodialysis is performed. This control could be affected manually or automatically through a programmed feedback operation.

Although a mechanism involving pumps driving the fluid is described, the inlet and outlet pump assemblies may be configured to allow different mechanisms for the phase-delay peaks.

One such mechanism involves the inlet pump assembly comprising an inlet pump 207 and the outlet pump assembly comprising an outlet valve 213. In this mechanism, the inlet pump 207 performs the dialysate delivery stroke, and the outlet valve 213 performs the dialysate removal stroke. In this mechanism, the outlet valve 213 operates in a similar manner to the outlet pump 216 operation described above. The inlet pump 207 may force fluid into the dialyser before the outlet valve 213 opens. Thus the mechanism utilises a single pump and a single valve.

Another such mechanism involves the inlet pump assembly comprising an inlet valve 209 and the outlet pump assembly comprising an outlet pump 216. In this mechanism, the inlet valve 209 performs the dialysate delivery stroke, and the outlet pump 216 performs the dialysate removal stroke. In this mechanism, the inlet valve 209 operates in a similar manner to the inlet pump 207 operation described above. The outlet pump 216 may start drawing fluid from the dialyser 12 before the inlet valve opens 209. Thus the mechanism utilises a single pump and a single valve.

Another such mechanism involves only an inlet pump 207 and an outlet pump 216 and no associated inlet or outlet valves 209, 213. In this mechanism, the inlet pump 207 performs the dialysate delivery stroke, and the outlet pump 216 performs the dialysate removal stroke. In this mechanism, as described previously, the inlet pump 207 delivery stroke may commence before the outlet pump 216 removal stroke commences. Equally, the inlet pump 207 delivery stroke may terminate before the outlet pump 216 removal stroke terminates.

It should be understood that, as described above, references to "operation of the device" do not require that the device is being operated in contact with a patient. There are various situations in which a blood treatment device could be operated in a phased convective operation which does not involve use for patient treatment. One example of such operation is during cleaning of the device. As outlined above, operating the device in a convective operation may clear particles or molecules that build up on the semi-permeable membrane of the dialyser. One other example of such operation is during a training exercise. One other example of such operation of the device is during calibration of the device.

It should be understood that various alternatives of the above-described embodiment may be possible.

Figure 7:
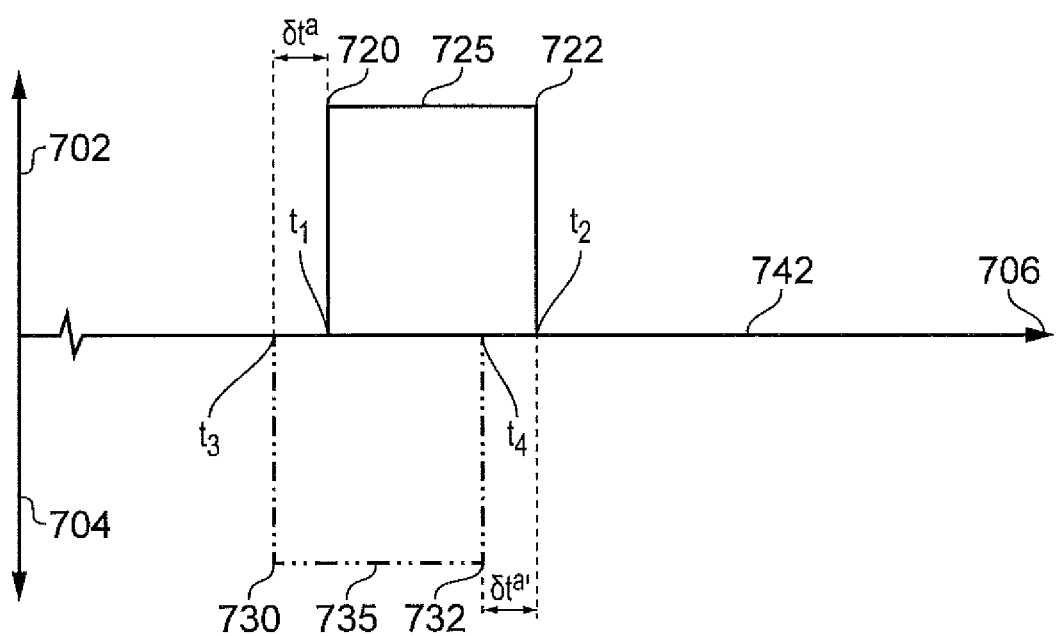
FIG. 7 an enlarged view of phase-advance operation, in which the outlet pump dialysate removal stroke commences before the inlet pump dialysate delivery stroke.

One alternative to the device mechanism described in FIGS. 5 and 6 is shown by FIG. 7. FIG. 7 shows the inlet pressure (solid line) and outlet pressure (dashed line) of phase-advance convective operation. Phase-advance convective operation operates is a type of phased convective operation in which, as shown by FIG. 7, each dialysate delivery stroke commencement time $t_1$ is after the respective corresponding dialysate removal stroke commencement time $t_3$ and before the respective corresponding dialysate removal stroke termination time $t_4$.

Figure 8:
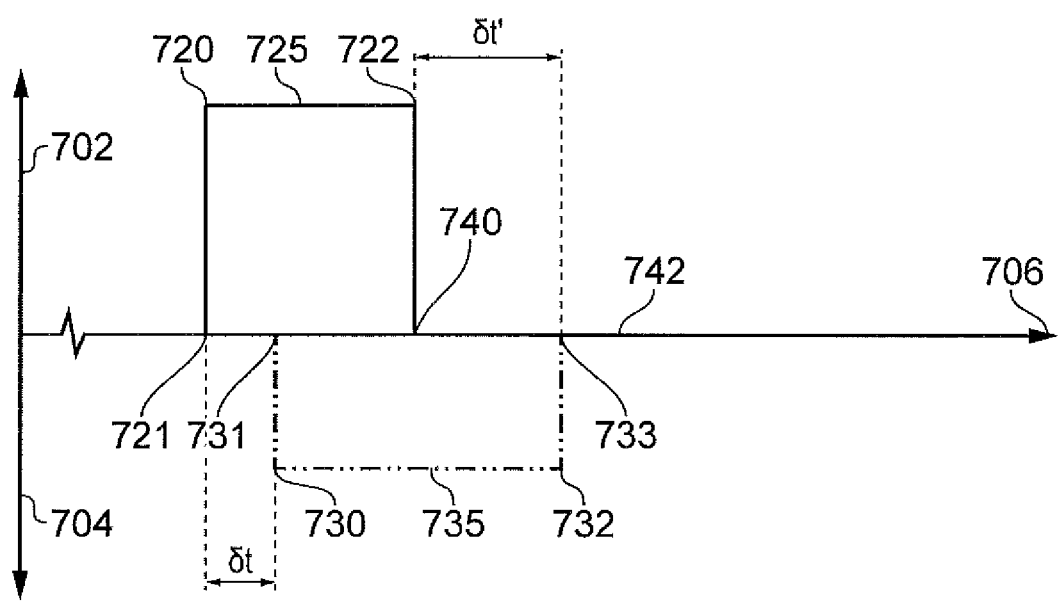
FIG. 8 is an enlarged view of an operation method, in which the outlet pump dialysate removal stroke has a longer duration than the inlet pump dialysate delivery stroke.

One other alternative to the device mechanism described in FIGS. 5 and 6 is that the difference between the starts and finishes of the inlet and outlet pump cycles may not be by the same amount δt. The difference between the start of the peaks may be δt, the difference between the ends of the peaks may be δt', wherein δt is longer than or shorter than δt'. Such an alternative is shown in FIG. 8, in which δt' is larger than δt. For comparison with FIG. 6, the same reference numerals have been used for both FIG. 6 and FIG. 8.

One other possible adaptation of the mechanism described above is that the pumps (termed "inlet" and "outlet" for clarity) may be swapped, so that the inlet pump 207 functions as an outlet pump 216 and the outlet pump 216 functions as an inlet pump 207. The terms "first" and "second" used to described the pumps with reference to FIGS. 1 and 2 can be replaced by "inlet" or "outlet" depending on their function.

Although a specific form of blood treatment apparatus has been provided by way of example, it should be appreciated that the phased convective method is applicable to various forms of blood treatment apparatus. By way of example, although a blood treatment apparatus having a disposable cartridge has been described, the method may be used with a non-disposable cartridge, or a blood treatment device which does not have a cartridge. Although operation of pumps has been described by means of pneumatic pumps, it should be understood that there are various possible ways for the pumps and valves to be actuated. Non-limiting examples include hydraulic or mechanical actuation means. The pumps and valves used should not be limited to those comprising a flexible membrane. Any form of pump or valve may be appropriate, for example a volumetric pump.

The invention claimed is:

1. A blood treatment device comprising:
a dialyser;
at least one inlet pump in fluid communication with the dialyser and operable according to an inlet pump cycle having a dialysate delivery stroke;
at least one outlet pump in fluid communication with the dialyser and operable according to an outlet pump cycle having a dialysate removal stroke; and
a control system configured to
operate the at least one inlet pump in the inlet pump cycle, and
operate the at least one outlet pump in the outlet pump cycle, wherein
each dialysate removal stroke begins after a respective corresponding dialysate delivery stroke begins and before the respective corresponding dialysate delivery stroke ends or each dialysate delivery stroke begins after a respective corresponding dialysate removal stroke begins and before the respective corresponding dialysate removal stroke ends.

2. The blood treatment device of claim 1, wherein each inlet pump dialysate delivery stroke begins at a commencement time t1 and ends at a termination time t2, and each outlet pump dialysate removal stroke begins at a commencement time t3 and ends at a termination time t4.

3. The blood treatment device of claim 1, wherein
the at least one inlet pump operates to deliver a first volume of dialysate from a dialysate source to the dialyser according to an inlet pump cycle having the dialysate delivery stroke,
and
the at least one outlet pump operates to remove a second volume of dialysate from the dialyser and deliver the dialysate away from the dialyser according to an outlet pump cycle having the dialysate removal stroke.

4. The blood treatment device of claim 3, wherein each inlet pump cycle includes a corresponding outlet pump cycle.

5. The blood treatment device of claim 2, wherein a duration between the commencement time t1 and the commencement time t3 is a fraction of either: the dialysate delivery stroke upon the commencement time t3 being between the commencement time t1 and the termination time t2, or the dialysate removal stroke upon the commencement time t1 being between the commencement time t3 and the termination time t4.

6. The blood treatment device of claim 5, wherein the fraction is: between 0.01 and 0.99, between 0.05 and 0.95, or between 0.10 and 0.80.

7. The blood treatment device of claim 1, wherein each dialysate delivery stroke is the same duration as its corresponding dialysate removal stroke, a first volume of a dialysate is delivered to the dialyser in one inlet pump cycle, a second volume of the dialysate is removed from the dialyser in one outlet pump cycle, the first volume of the dialysate is substantially the same as the second volume of the dialysate.

8. The blood treatment device of claim 1, wherein at least one of the at least one inlet pump and the at least one outlet pump comprises an assembly.

9. The blood treatment device of claim 1, wherein each of the inlet pump and outlet pump are independently operable between an open position and a closed position.

10. The blood treatment device of claim 1, wherein each of the inlet pump and the outlet pump are defined in part by a flexible membrane being independently operable between an open position and a closed position for each of the at least one inlet pump and the at least one outlet pump.

11. The blood treatment device of claim 9, wherein the inlet pump cycle begins from an inlet pump open position.

12. The blood treatment device of claim 9, wherein the outlet pump cycle begins from an outlet pump closed position.

13. The blood treatment device of claim 9, wherein the inlet pump includes a dialyser inlet valve and the outlet pump includes a dialyser outlet valve.

14. The blood treatment device of claim 13, wherein each of the dialyser inlet valve and the dialyser outlet valve are independently operable between an open position and a closed position.

15. The blood treatment device of claim 1, wherein each of the inlet pump and the outlet pump are defined at least in part by a flexible membrane independently operable between an open position and a closed position for each of the at least one inlet pump and the at least one outlet pump.

16. The blood treatment device of claim 1, wherein the at least one inlet pump and the at least one outlet pump are each operable to deliver a volume of dialysate from a dialysate source to the dialyser and remove a volume of the dialysate from the dialyser.

17. The blood treatment device of claim 16, wherein the control system is configured to alternate between the at least one inlet pump and the at least one outlet pump after a given number of inlet pump cycles.

18. The blood treatment device of claim 17, wherein the number of inlet pumping cycles is two or more inlet pumping cycles.

19. The blood treatment device of claim 1, wherein the inlet pump and the outlet pump are arranged to pump a predetermined volume of dialysate.

20. The blood treatment device of claim 1, wherein the inlet pump and the outlet pump are included on a disposable cartridge.

21. The blood treatment device of claim 20, wherein at least one of a dialyser inlet valve or a dialyser outlet valve is included on the disposable cartridge.

22. The blood treatment device of claim 20, wherein the inlet pump, the outlet pump, a dialyser inlet valve and a dialyser outlet valve, each included on the disposable cartridge, are operated by actuation of a flexible membrane by negative and/or positive air pressure.

23. A blood treatment device comprising:

a dialyser;

at least one inlet pump in fluid communication with the dialyser, the at least one inlet pump operable according to an inlet pump cycle having a dialysate delivery stroke;

at least one outlet pump configured to operate according to an outlet pump cycle having a dialysate removal stroke; and a control system configured to operate the at least one inlet pump in the inlet pump cycle, and operate the at least one outlet pump in the outlet pump cycle, wherein at least one dialysate removal stroke begins after a corresponding dialysate delivery stroke begins and before the corresponding dialysate delivery stroke ends, or at least one dialysate delivery stroke begins after a corresponding dialysate removal stroke begins and before the corresponding dialysate removal stroke ends.

* * * * *